United States Patent
Parker et al.

(10) Patent No.: US 8,526,641 B2
(45) Date of Patent: *Sep. 3, 2013

(54) CUSTOMIZABLE MASS ARRANGEMENTS FOR BONE CONDUCTION DEVICES

(75) Inventors: John L. Parker, Roseville (AU); Derek Ian Darley, Cromer Heights (AU)

(73) Assignee: Cochlear Limited, Macquarie University, NSW (AU)

( * ) Notice: Subject to any disclaimer, the term of this patent is extended or adjusted under 35 U.S.C. 154(b) by 1274 days.

This patent is subject to a terminal disclaimer.

(21) Appl. No.: 12/167,728

(22) Filed: Jul. 3, 2008

(65) Prior Publication Data

US 2009/0247810 A1 Oct. 1, 2009

Related U.S. Application Data

(60) Provisional application No. 61/041,185, filed on Mar. 31, 2008.

(51) Int. Cl.
*H04R 25/00* (2006.01)
*A61N 1/00* (2006.01)

(52) U.S. Cl.
USPC .......... 381/151; 381/326; 381/380; 381/418; 600/25; 607/55; 607/57

(58) Field of Classification Search
USPC .................. 381/151, 326, 380, 418; 600/25; 607/55, 57
See application file for complete search history.

(56) References Cited

U.S. PATENT DOCUMENTS

| | | | | |
|---|---|---|---|---|
| 2,045,404 A | * | 6/1936 | Nicholides | 381/151 |
| 3,733,445 A | * | 5/1973 | Sebesta et al. | 381/418 |
| 4,612,915 A | * | 9/1986 | Hough et al. | 600/25 |
| 4,904,233 A | * | 2/1990 | H.ang.kansson et al. | 600/25 |
| 5,015,225 A | | 5/1991 | Hough et al. | |
| 5,460,593 A | * | 10/1995 | Mersky et al. | 600/25 |
| 5,771,298 A | * | 6/1998 | Davis et al. | 381/60 |
| 5,949,895 A | * | 9/1999 | Ball et al. | 381/326 |

(Continued)

FOREIGN PATENT DOCUMENTS

| WO | WO 96/21335 | 7/1996 |
|---|---|---|
| WO | WO 01/93635 | 12/2001 |

(Continued)

OTHER PUBLICATIONS

International Application No. PCT/US201 0/028706, International Search Report mailed on May 20, 2010 (2 pages).

(Continued)

*Primary Examiner* — Long K Tran
*Assistant Examiner* — Jordan Klein
(74) *Attorney, Agent, or Firm* — Kilpatrick, Townsend & Stockton, LLP

(57) ABSTRACT

A bone conduction device, comprising: a sound input element configured to receive an acoustic sound signal; an electronics module configured generate an electrical signal representing said acoustic sound signal; and a transducer configured to generate motion of a mass component based on said electrical signal so as to generate one or more mechanical forces resulting in one or more of motion and vibration of a recipient's skull thereby causing sound perception, wherein one or more of the size and shape of said mass component is selectable at least partially based on a desired mechanical force to be generated by said transducer.

20 Claims, 10 Drawing Sheets

(56) References Cited

U.S. PATENT DOCUMENTS

| | | | |
|---|---|---|---|
| 6,123,660 A | 9/2000 | Leysieffer | |
| 6,190,305 B1 | 2/2001 | Ball et al. | |
| 6,554,761 B1* | 4/2003 | Puria et al. | 600/25 |
| 6,885,753 B2* | 4/2005 | Bank | 381/326 |
| 7,065,223 B2* | 6/2006 | Westerkull | 381/326 |
| 7,149,318 B2* | 12/2006 | Bank et al. | 381/190 |
| 7,214,179 B2* | 5/2007 | Miller et al. | 600/25 |
| 7,242,786 B2* | 7/2007 | .ANG.snes | 381/326 |
| 7,442,164 B2* | 10/2008 | Berrang et al. | 600/25 |
| 7,564,988 B2* | 7/2009 | Azima et al. | 381/326 |
| 7,724,911 B2* | 5/2010 | Menzel et al. | 381/151 |
| 7,840,020 B1* | 11/2010 | Miller et al. | 381/326 |
| 2004/0236176 A1 | 11/2004 | Asnes | |
| 2006/0098829 A1* | 5/2006 | Kobayashi | 381/151 |
| 2007/0053536 A1* | 3/2007 | Westerkull | 381/326 |
| 2007/0156011 A1* | 7/2007 | Westerkull | 600/25 |
| 2008/0292125 A1 | 11/2008 | Asnes | |
| 2009/0023109 A1 | 1/2009 | Jinton et al. | |
| 2009/0245553 A1 | 10/2009 | Parker | |
| 2010/0208924 A1* | 8/2010 | Westerkull | 381/318 |

FOREIGN PATENT DOCUMENTS

| | | |
|---|---|---|
| WO | WO 03/001845 | 1/2003 |
| WO | WO 03/001846 | 1/2003 |
| WO | WO 2006/088410 | 8/2006 |

OTHER PUBLICATIONS

International Application No. PCT/US2010/028706, Written Opinion mailed on May 20, 2010 (4 pages).

International Application No. PCT/US201 0/028706, International Preliminary Report on Patentability mailed on Sep. 27, 2011 (5 pages).

European Application No. 09728994.6, Extended European Search Report mailed on May 30, 2011 (6 pages).

International Application No. PCT/AU2009/000367, International Search Report mailed on Jul. 30, 2009 (4 pages).

International Application No. PCT/AU2009/000367, Written Opinion mailed on Jul. 30, 2009 (5 pages).

International Application No. PCT/AU2009/000367, International Preliminary Report on Patentability mailed on Oct. 5, 2010 (6 pages).

* cited by examiner

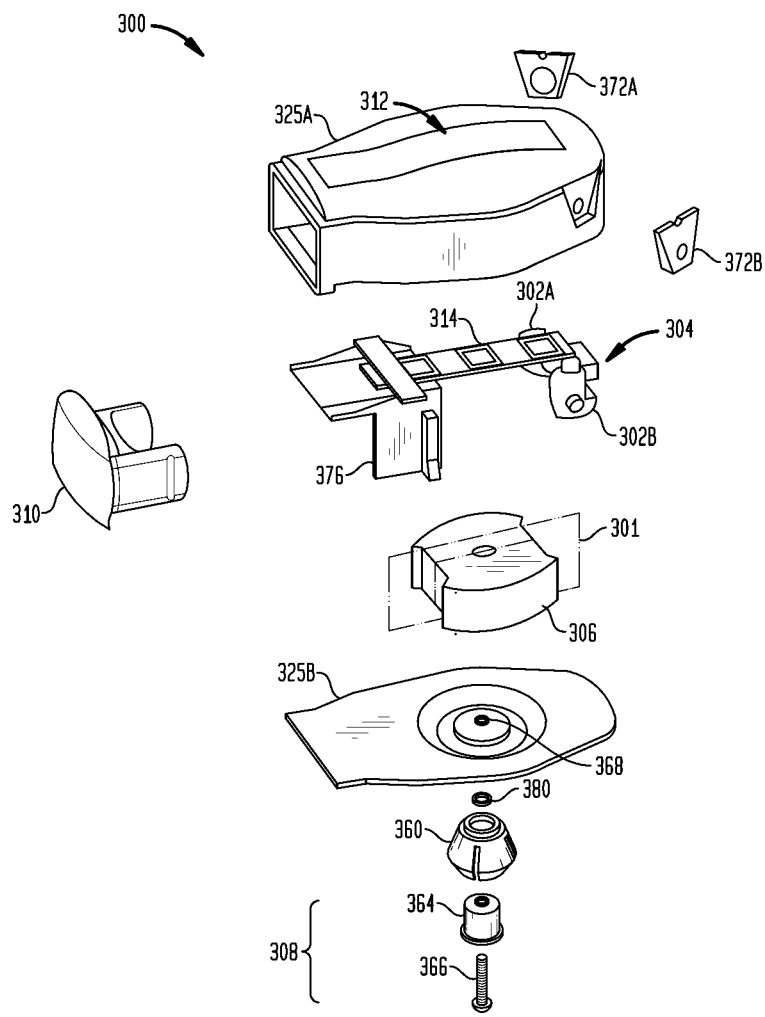

CUSTOMIZABLE MASS ARRANGEMENTS FOR BONE CONDUCTION DEVICES

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention relates generally to prosthetic hearing devices, and more particularly, to bone conduction devices having customizable mass arrangements.

2. Related Art

There are three basic types of hearing loss: sensorineural, conductive, and mixed hearing losses. Sensorineural hearing loss results from damage to the inner ear or to the nerve pathways from the inner ear to the brain. The majority of human sensorineural hearing loss is caused by abnormalities or damage to the hair cells in the cochlea. Hair cells in the cochlea are the sensory receptors that transduce sound to nerve impulses. Acoustic hearing aids may be appropriate for those who suffer from mild to moderate sensorineural hearing loss. In cases of severe or profound sensorineural hearing loss, a cochlear implant may be the appropriate choice. Cochlear implants bypass the hair cells in the cochlea and directly stimulate the auditory nerve fibers in the cochlea by an electrode array that is implanted in the cochlea. Simulation of the auditory nerve fibers creates the sensation of hearing in the recipient.

Conductive hearing loss occurs when there is a problem with the conduction of sound from the external or middle ear to the inner ear. This type of hearing loss may be caused by anything that impedes the motion of the ossicles, the three bones of the middle ear that conduct sound to the cochlea. It may also be caused by a failure of the eardrum to vibrate in response to sound or fluid in the middle ear. Conductive hearing loss may be treated by acoustic hearing aids, middle ear implants, and the like.

Still other individuals suffer from mixed hearing losses, that is, conductive hearing loss in conjunction with sensorineural hearing. In other words, there may be damage in both the outer or middle ear and the inner ear (cochlea) or auditory nerve.

While many individuals suffering from conductive hearing loss often use acoustic hearing aids, such hearing aids may not be suitable for all individuals, such as those suffering from chronic ear infections or from single-sided deafness. An alternative treatment is the use of bone conduction hearing aids, or simply conduction devices herein.

Bone conduction hearing aids utilize the bones of an individual's skull to transmit acoustic signals to the cochlea. Generally, most bone conduction hearing aids function by converting a received sound signal into a mechanical vibration. This vibration is then transferred to the bone structure of the skull. This skull vibration results in motion of the fluid of the cochlea, thereby stimulating the cochlear hair cells and causing the perception of sound in the recipient.

Bone conduction devices may be attached to a titanium implant implanted in a recipient's skull, via an external abutment. The titanium implant is surgically implanted into the part of the skull bone that is behind the ear and allowed to naturally integrate with the skull bone over time. The bone conduction device is coupled to the titanium implant via the external abutment. Mechanical vibrations from the bone conduction device are then transmitted to the skull through the external abutment and the titanium implant to stimulate nerve fibers of the inner ear of the recipient.

Some bone conduction devices generally have a bulky profile, as there are a large number of components within the devices, each component taking up a substantial amount of space and position. Bone conduction devices having bulky profiles may impact daily performance or use by the recipient, since a bulky device attached to the head or other body parts of the recipient may interfere with the recipient's movements or activities.

SUMMARY

In one aspect of the present invention, a bone conduction device is provided. The device comprises: a sound input element configured to receive an acoustic sound signal; an electronics module configured generate an electrical signal representing said acoustic sound signal; and a transducer configured to generate motion of a mass component based on said electrical signal so as to generate one or more mechanical forces resulting in one or more of motion and vibration of a recipient's skull thereby causing sound perception, wherein one or more of the size and shape of said mass component is selectable at least partially based on a desired mechanical force to be generated by said transducer.

In another aspect of the present invention, a hearing rehabilitation system is provided. The system comprises: a bone conduction device, comprising: a sound input element configured to receive an acoustic sound signal; an electronics module configured generate an electrical signal representing said acoustic sound signal; and a transducer configured to generate motion of a mass component based on said electrical signal so as to generate one or more mechanical forces resulting in one or more of motion and vibration of a recipient's skull thereby causing sound perception, wherein one or more of the size and shape of said mass component is selectable at least partially based on a desired mechanical force to be generated by said transducer, and an anchor configured to be attached to the recipient's skull and further configured to transfer said mechanical forces from said transducer to the recipient's skull.

In a further aspect of the present invention, a bone conduction kit is provided. The kit comprises: first and second mass components; and a bone conduction device, comprising: a sound input element configured to receive an acoustic sound signal; an electronics module configured generate an electrical signal representing said acoustic sound signal; and a transducer configured to have at least one of said first and second mass components positioned therein, configured to generate motion of said at least one mass component therein based on said electrical signal so as to generate one or more mechanical forces resulting in one or more of motion and vibration of a recipient's skull thereby causing sound perception, wherein which of said first or second mass components to be positioned in said transducer is selected at least partially based on a desired mechanical force to be generated by said transducer.

BRIEF DESCRIPTION OF THE DRAWINGS

Illustrative embodiments of the present invention are described herein with reference to the accompanying drawings, in which:

FIG. 3 is an exploded view of an embodiment of a bone conduction device in accordance with embodiments of the present invention;

DETAILED DESCRIPTION

Embodiments of the present invention are generally directed to a bone conduction device for converting a received acoustic sound signal into a mechanical force delivered via a recipient's skull to the recipient's hearing organs. The bone conduction device receives the acoustic sound signal and generates an electrical signal representing the acoustic sound signal. The bone conduction device includes a transducer which converts the electrical signal into motion of a mass component so as to generate one or more mechanical forces resulting in one or more of motion and vibration of a recipient's skull causing perception of said acoustic signal by the recipient.

In certain embodiments of the present invention, rather than having a dedicated mass (also referred to herein as a "mass component") mounted thereto, the transducer has a functional component attached thereto which is used by the transducer to generate the mechanical forces, in addition to performing its own function. In some embodiments, in addition to the functional component acting as an alternative mass component, supplemental mass component may be mounted to the transducer or the alternative mass component.

In other embodiments of the present invention, a dedicated mass component or a functional component acting as a mass component may formed into any one of many different sizes, shapes and configurations, based on, for example, the desired mechanical force, recipient characteristics, and/or the needs of a specific recipient. In one such embodiment of the present invention, the mass component may be formed as two bilateral extensions. In yet further embodiments of the present invention, a pair of additional dedicated mass components or functional components may be coupled at the outer ends of bilateral extensions fixed to the transducer at the center of the bilateral extensions.

In various embodiments of the present invention, the transducer may comprise a piezoelectric element that deforms in response to application of the electrical signal thereto, thereby generating mechanical forces, or vibrations, which are transferred to the recipient's skull to produce bone conduction of the mechanical forces which represent the acoustic sound signal. The amount of deformation of a piezoelectric element in response to an applied electrical signal depends on material properties of the element, orientation of the electric field with respect to the polarization direction of the element, geometry of the element, etc.

Figure 1:
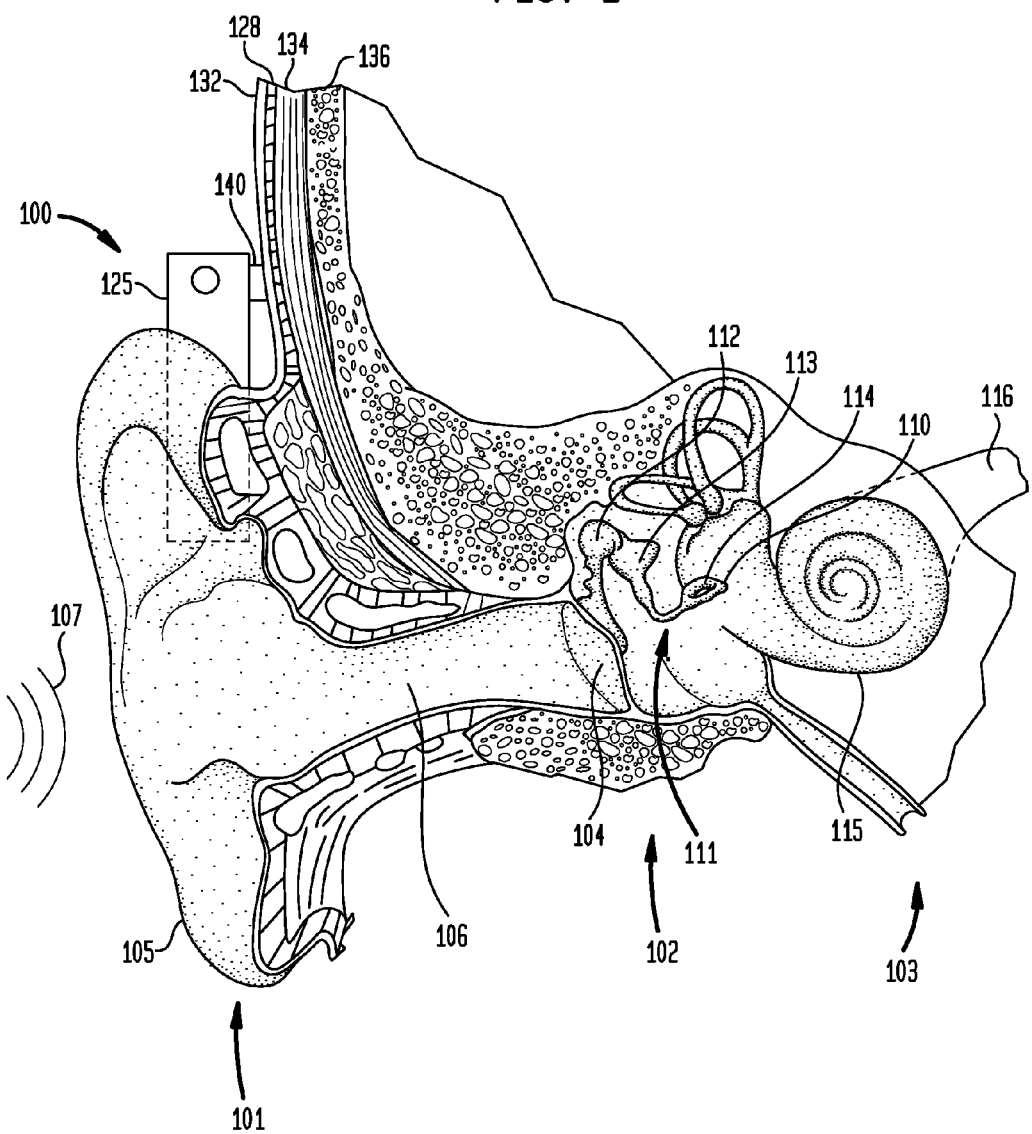
FIG. 1 is a perspective view of a bone conduction device implanted behind a recipient's ear.

FIG. 1 is a perspective view of embodiments of a bone conduction device 100 in which embodiments of the present invention may be advantageously implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient. In the embodiment illustrated in FIG. 1, bone conduction device 100 comprises a housing 125 having a microphone (not shown) positioned therein or thereon. Housing 125 is coupled to the body of the recipient via coupling 140 and an anchor system (not shown). As described below, bone conduction device 100 may comprise a sound processor, a transducer, transducer drive components and/or various other electronic circuits/devices. In accordance with embodiments of the present invention, an anchor system (not shown) may be implanted in the recipient. As described below, the anchor system may be fixed to bone 136 and may extend from bone 136 through muscle 134, fat 128 and skin 132 so that coupling 140 may be coupled to the anchor system.

Figure 2A:
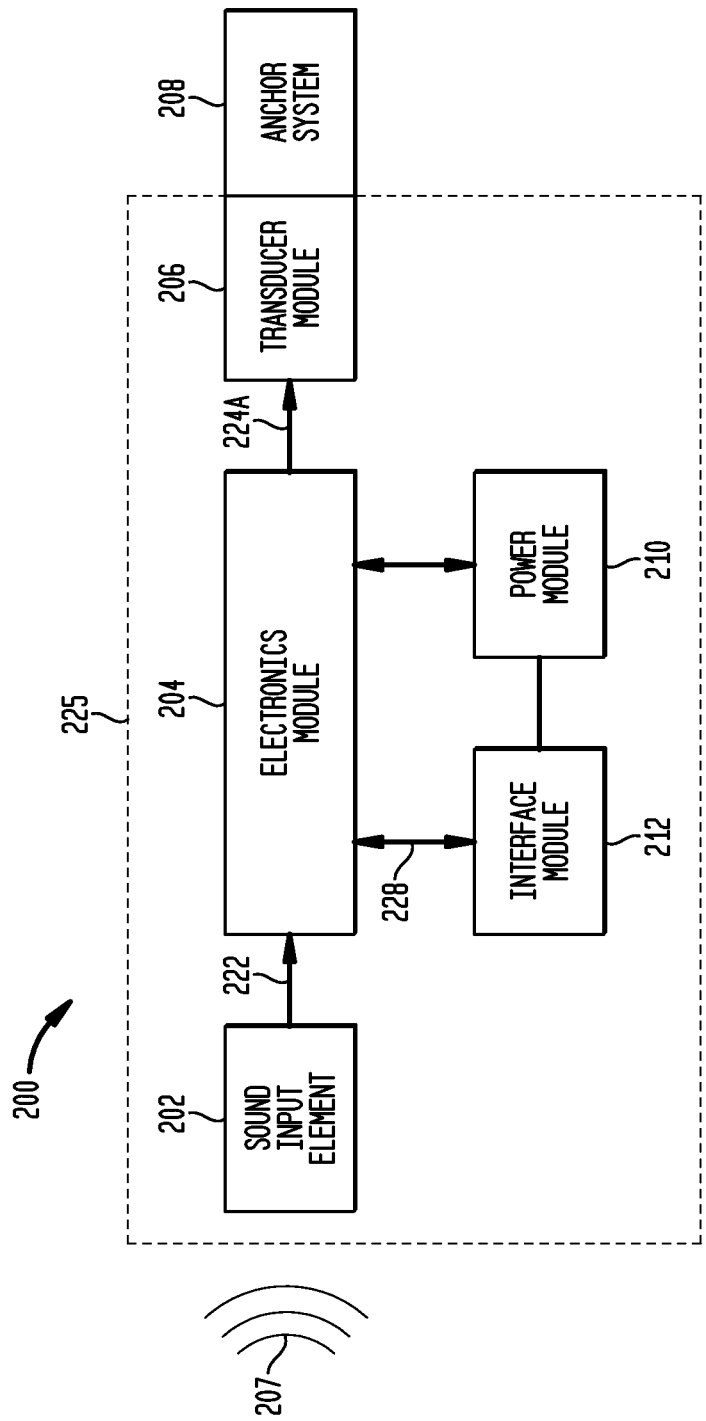
FIG. 2A is a high-level functional block diagram of a bone conduction device, such as the bone conduction device of FIG. 1.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224A. As described below in more detail, electronics module 204 may include a sound processor, control electronics, transducer drive components, and a variety of other elements.

As shown in FIG. 2A, transducer 206 receives adjusted electrical signal 224A and generates a mechanical output force that is delivered to the skull of the recipient via coupling 140, shown in FIG. 2A as anchor system 208, that is coupled to bone conduction device 200. Delivery of this output force causes one or more of motion or vibration of the recipient's skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer 206, power module 210 and interface module 212 have all been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

In embodiments of the present invention, transducer 206 may be one of many types and configurations of transducers, now known or later developed. In one embodiment of the present invention, transducer 206 may comprise a piezoelectric element which is configured to deform in response to the application of electrical signal 224. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz (SiO2), Berlinite (AlPO4), Gallium orthophosphate (GaPO4) and Tourmaline. Exemplary piezoelectric ceramics include barium titanate (BaTiO30), lead zirconate titanate (PZT), or zirconium (Zr).

Some piezoelectric materials, such as barium titanate and PZT, are polarized materials. When an electric field is applied across these materials, the polarized molecules align themselves with the electric field, resulting in induced dipoles within the molecular or crystal structure of the material. This alignment of molecules causes the deformation of the material.

In other embodiments of the present invention, other types of transducers may be used. For example, various motors configured to operate in response to electrical signal 224 may be used.

Figure 2B:
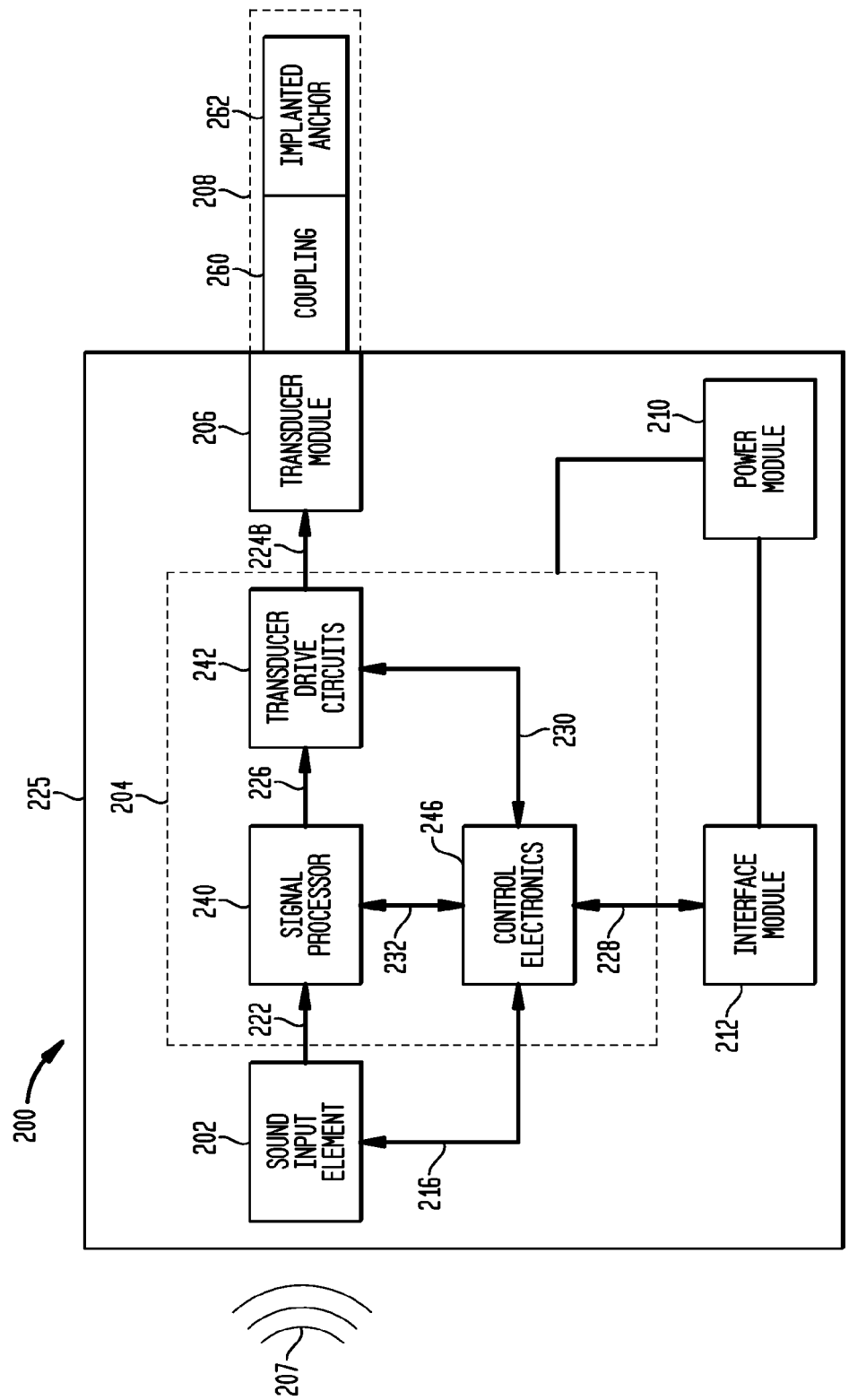
FIG. 2B is detailed functional block diagram of the bone conduction device illustrated in FIG. 2A.

In one embodiment of the present invention, transducer 206 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 208. In one embodiment of the present invention, anchor system 208 comprises one or more external magnets 260 which magnetically couples to one or more implanted magnets 262, as illustrated in FIG. 2B. In the embodiment illustrated in FIG. 2A, external magnets 260 are configured to be attached to housing 225. As such, in this embodiment, vibration from transducer 206 is provided to external magnets 260 through housing 225.

In certain embodiments of the present invention, electronics module 204 includes a printed circuit board (PCB) to electrically connect and mechanically support the components of electronics module 204. Sound input element 202 may comprise one or more microphones (not shown) and is attached to the PCB.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 226. In certain embodiments, sound processor 240 may comprise substantially the same sound processor as is used in an air conduction hearing aid. In further embodiments, sound processor 240 comprises a digital signal processor.

Processed signal 226 is provided to transducer drive components 242. Transducer drive components 242 output a drive signal 224B, to transducer 206. Based on drive signal 224B, transducer 206 provides the output force to the skull of the recipient.

For ease of description the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, in one embodiment of the present invention, anchor system 208 comprises an external magnet 260 which magnetically couples to an implanted magnet 262. External magnet 260 may be attached to one or more of transducer 206 or housing 225. For example, in certain embodiments, external magnet 260 is attached to transducer 206 and vibration is received directly therefrom. In other embodiments, external magnet 260 is attached to housing 225 and vibration is applied from transducer 206 through housing 225 to external magnet 260. According to one embodiment of the present invention in which coupling 140 comprises external magnet 260, the vibration received by external magnet 260 from transducer 206 causes external magnet 260 to vibrate. Since, according to this embodiment of the present invention, external magnet 260 is magnetically coupled to implanted magnet 262, the magnetic forces coupling external magnet 260 and implanted magnet 262 vibrates accordingly. The vibration, communicated from external magnet 260 to implanted magnet 262 magnetically, is then transferred from implanted magnet 262 to the recipient's bone 136.

As noted above, a recipient may control various functions of the device via interface module 212. Interface module 212 includes one or more components that allow the recipient to provide inputs to, or receive information from, elements of bone conduction device 200.

As shown, control electronics 246 may be connected to one or more of interface module 212, sound pickup device 202 (via signal 216), sound processor 240 (via signal 232) and/or transducer drive components 242 (via signal 230). In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, included within electronics module 304 are a sound processor, transducer drive components and control electronics. For ease of illustration, these components have not been illustrated in FIG. 3.

In the illustrated embodiment, electronics module 304 includes a printed circuit board 314 (PCB) to electrically connect and mechanically support the components of electronics module 304. Attached to PCB 314 are one or more sound input elements, shown as microphones 302A and 302B to receive a sound.

In the embodiment illustrated in FIG. 3, bone conduction device 300 further includes a two-part housing 325, comprising first housing portion 325A and second housing portion 325B. Bone conduction device 300 further includes a third housing portion 310 that interfaces with element 376. Housing portions 325 are configured to mate with one another to substantially seal bone conduction device 300. Microphone covers 372A and 372B are releasably attached to first housing portion 325A. Microphone covers 372A and 372B provide a barrier over microphones 302A and 302B to protect microphones 302A and 302B from dust, dirt or other debris.

Bone conduction device 300 further includes an embodiment of interface module 212, referred to herein as interface module 312. Interface module 312 is configured to provide or receive user inputs from the recipient. A power supply or battery (not shown) may be included in bone conduction 300 to supply power to the various components.

Also as shown in FIG. 3, bone conduction device 300 comprises a transducer 306 which is symmetrical about plane 301. Transducer 306 generates an output force that causes movement of the cochlea fluid so that a sound may be perceived by the recipient. The output force results in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360, anchor 366 and abutment 364. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 366. Implanted anchor 366 may comprise a bone screw 366 implanted in the skull of the recipient. In an implanted configuration, screw 366 protrudes from the recipient's skull through the skin. Abutment 364 is attached to screw 366 above the recipient's skin. In embodiments, abutment 364 and screw 366 may be integrated into a single implantable component. Coupling 360 is configured to be releasably attached to abutment 364 to create a vibratory pathway between transducer 306 and the skull of the recipient.

In alternative embodiments of the present invention, bone conduction device 300 may comprise one or more additional sound input element. For example, bone conduction device 300 may comprises an electrical input. In such embodiments, the electrical input is configured to connect device 300 to external equipment and receive an electrical sound signal directly therefrom. Electrical input 316 may permit bone conduction device 300 to be connected to, for example, AM/FM radios, MP3 players, televisions, mobile phones, etc.

In still other embodiments, a further sound input element in the form of a telecoil may be integrated in, or connected to, bone conduction device 300. Such a telecoil permits bone conduction device 300 to receive input signals from, for example, a telephone or other similar device.

Figure 4:
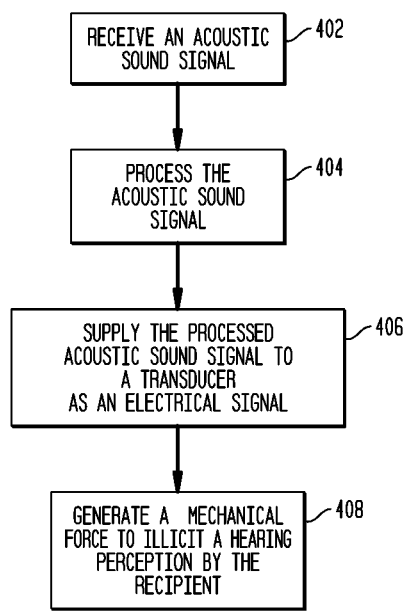
FIG. 4 is a flowchart illustrating the conversion of an input sound into skull vibration in accordance with embodiments of the present invention.

FIG. 4 illustrates the conversion of an input acoustic sound signal into a mechanical force for delivery to the recipient's skull in accordance with embodiments of bone conduction device 300. At block 402, bone conduction device 300 receives an acoustic sound signal. In certain embodiments, the acoustic sound signal is received via microphones 302. In other embodiments, the input sound is received via an electrical input. In still other embodiments, a telecoil integrated in, or connected to, bone conduction device 300 may be used to receive the acoustic sound signal.

At block 404, the acoustic sound signal received by bone conduction device 300 is processed by the speech processor in electronics module 304. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 300.

At block 406, the processed sound signal is provided to transducer 306 as an electrical signal. At block 408, transducer 306 converts the electrical signal into a mechanical force configured to be delivered to the recipient's skull via anchor system 308 so as to illicit a hearing perception of the acoustic sound signal.

Figure 5:
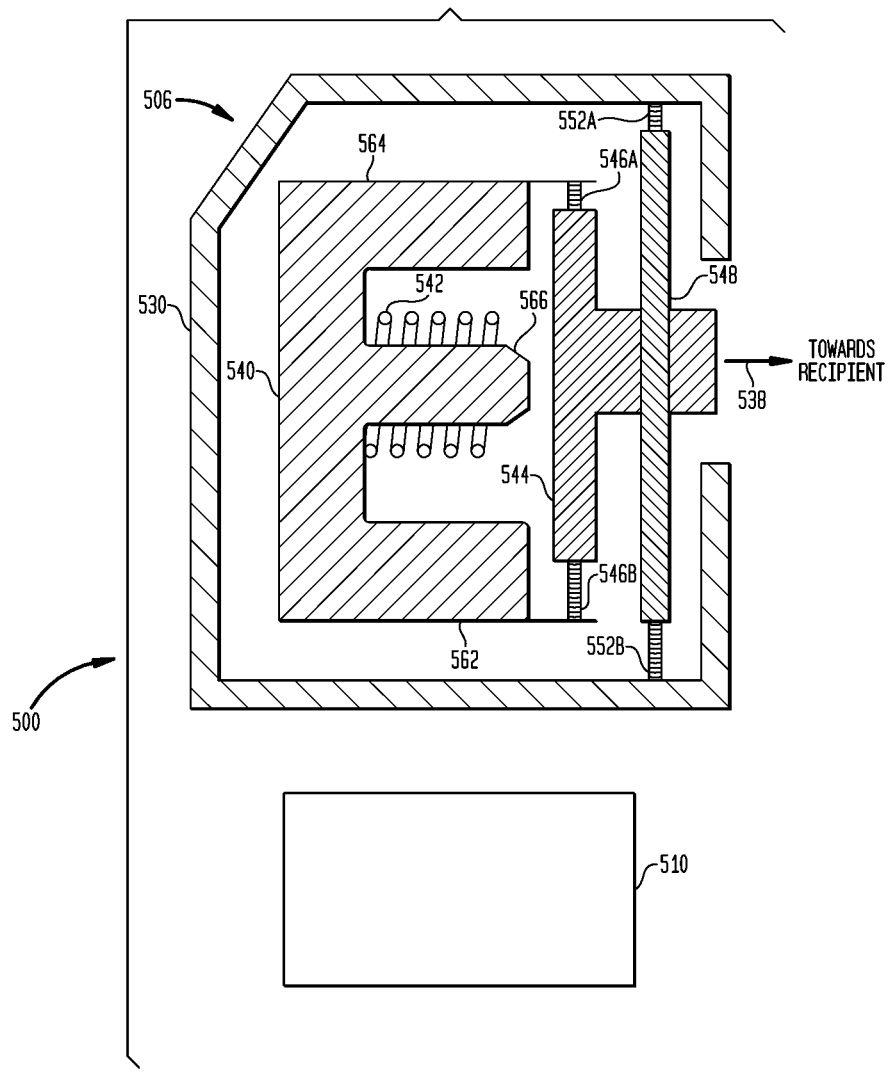
FIG. 5 is a cross-sectional view of components of a bone conduction device in which the transducer is remotely positioned from a battery.

FIG. 5 is a cross-sectional view of components of a bone conduction device in which a transducer is remotely positioned from a battery. Bone conduction device 500 comprises transducer 506 having housing 530 having disposed therein a magnet 540 having a primary magnet extension arm 566 and secondary magnetic extension arms 562, 564 as illustrated. Magnet 540 is configured such that when coil 542 is energized with an adjusted electrical signal, such as described above, magnet 540 and its primary and secondary extension arms 566, 562, 564 move in the direction of vibration output element 544. By varying the adjusted electrical signal, a rapid movement towards and away from the recipient (as indicated by direction arrow 538) is generated, thereby providing controlled mechanical forces in the direction of the recipient.

Primary springs 546A and 546B (collectively referred to as primary springs 546) mechanically couple magnet 540 to vibration output element 544. Element 544 in turn is coupled to transducer support element 548, which is itself mechanically coupled to housing 530 by means of secondary springs 552A and 552B (collectively referred to as secondary springs 552). Although not shown in FIG. 5, one end of vibration output element 544 is mechanically coupled to an anchor system, as described above with reference to FIG. 2. It should further be noted that although secondary springs 552 couple transducer support element 548 to housing 530, the springs are selected and/or arranged such that the majority of the generated vibratory forces from magnet 540 and vibration output element 544 are directed towards the recipient rather than to housing 530. In other words, primary springs 546 allow for the mechanical forces to be generated, as magnet 540 and vibration output element 546 and rapidly caused to move towards and away from each other, while secondary springs 552 allow the generated mechanical forces to be substantially directed to the recipient's bone by releasing transducer support element 548 to move substantially free from housing 530. As can be seen in the bone conduction device illustrated in FIG. 5, magnet 540 is a dedicated magnetic mass element while battery 510 is separate from magnet 540 and does not act as a mass for transducer 506.

Figure 6:
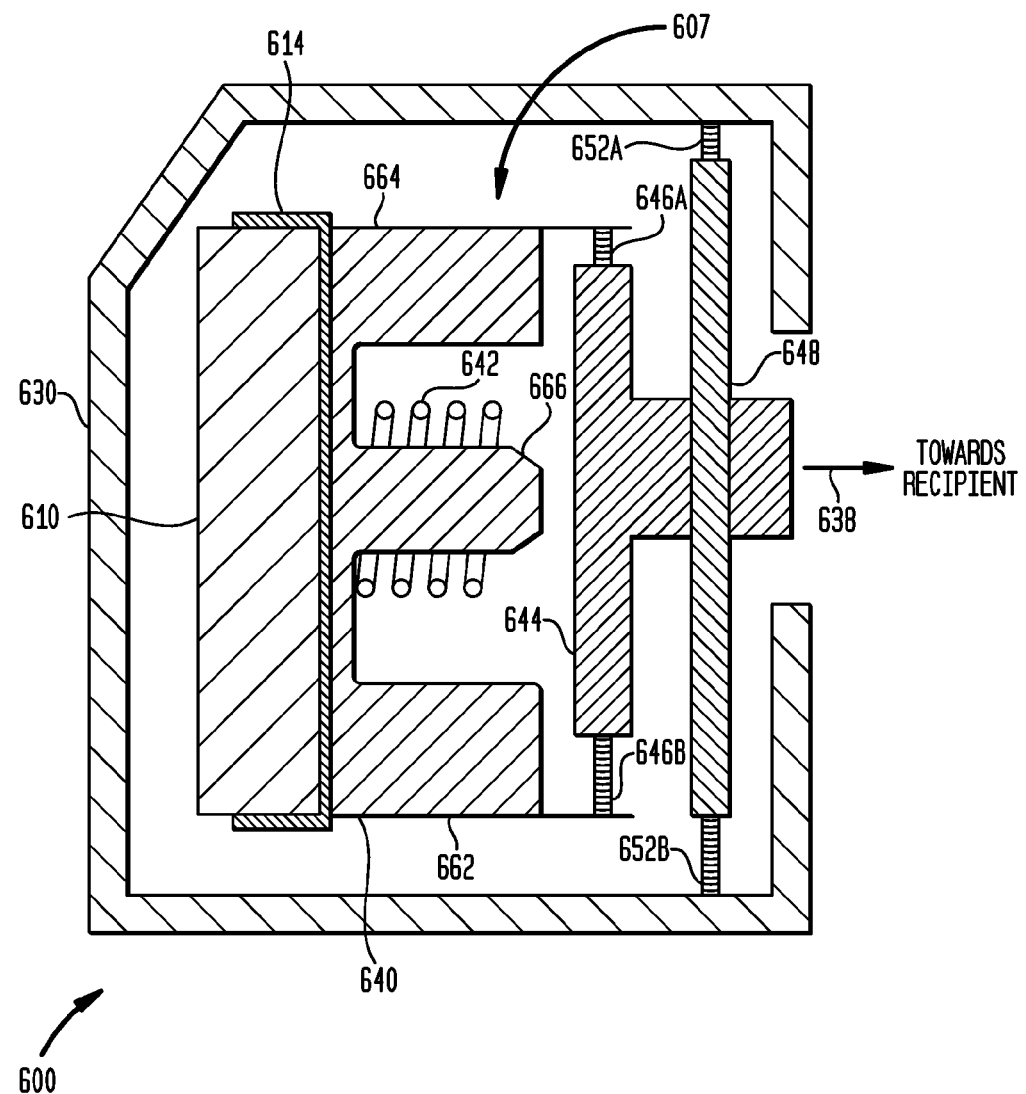
FIG. 6 is a cross-sectional view of components of a bone conduction device in accordance with embodiments of the present invention.

FIG. 6 is a cross-sectional view of components of a bone conduction device 600 in accordance with embodiments of the present invention. As may be seen, bone conduction device 600 includes a housing 630. The various components illustrated in FIG. 6 are largely similar to those described in conjunction with the device illustrated in FIG. 5. For example, springs 646A and 646B correspond to springs 546A and 546B. However, in the embodiment of the present invention shown in FIG. 6, the mass provided by magnet 640 substantially includes the mass from one or more other functional components, namely battery retention element 614 and battery 610 which are attached to magnet 640. Unlike the device illustrated in FIG. 5, where battery 510 and magnet 540 were physically separate and operationally independent of one another, in the embodiment illustrated in FIG. 6, by being attached to magnet 640, battery 610 adds its own mass to that of magnet 640 such that during operation, transducer 607 generates mechanical forces based on the combined mass of magnet 640 as well as battery 610. By adding the mass of battery 610 to transducer 607, the mass of magnet 640 may be substantially reduced. During operation, battery 610 continues to perform its own function of providing power to transducer 607 and other components of the bone conduction device. It is to be understood that various alternative masses may be used in embodiments of the present invention and that such alternative masses should not be limited to battery 610. Furthermore, it is to be understood that various mechanisms for retaining alternative masses may be used, as will be obvious to persons having skill in the art. For example, tabs, clips, screws, adhesives, compression fit and many others may be used to securely retain battery 610 in battery retention element 614.

Furthermore, although the embodiment depicted in FIG. 6 includes secondary magnetic extension arms 662, 664, in other embodiments of the present invention, magnet 640 may comprise only a primary magnetic extension arm 666. Furthermore, in other embodiments of the present invention, secondary magnetic extension arms 662, 664 may comprise additional arms or may have a different configuration. For example, in such embodiments, secondary magnetic extension arms may comprise a substantially cylindrical extension (not shown) disposed around primary magnetic extension arm 666. As described in conjunction with FIG. 5, aside from an alternative mass being used, coil 642 is repeatedly energized to cause magnet 640 and vibration output element 644 to be attracted to one another. The momentum of those attraction forces generates mechanical forces in the form of vibration, which is transferred to transducer support element 648. As described above, secondary springs 652A and 652B (collectively referred to as secondary springs 652) allow transducer support element 638 to then communicate the vibration mechanical forces to the recipient's bone.

Figure 7:
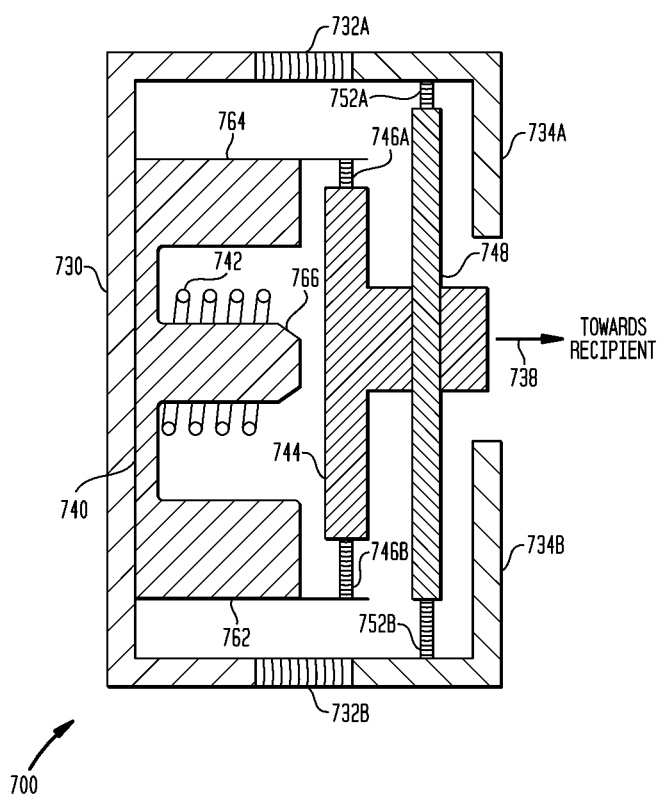
FIG. 7 is a cross-sectional view of components of a bone conduction device in accordance with embodiments of the present invention.

FIG. 7 is a cross-sectional view of components of a bone conduction device 700 in accordance with embodiments of the present invention. In the embodiment illustrated in FIG. 7, a first housing portion 730 is mounted or otherwise coupled to magnet 740 such that first housing portion 730 acts as a mass for the transducer. As such, first housing portion 730 is used by the transducer to generate the output forces for delivery to the recipient's skull. By adding the mass of first housing portion 730, the mass of magnet 740, which includes secondary magnet extension arms 762 and 764 and primary magnet extension arm 766, may be substantially reduced. As may be seen, bone conduction device 700 includes springs 746A and 746B which correspond to springs 546A and 546B of the embodiment of FIG. 5. As may be seen, element 744 is coupled to transducer support element 748, which is itself mechanically coupled to housing 730 by means of secondary springs 752A and 752B (collectively referred to as secondary springs 752).

In the embodiment shown in FIG. 7, flexible housing portions 732A and 732B (collectively referred to as flexible housing portions 732) may be provided to allow magnet 740 and first housing portion 730 to move towards vibration output element 744 as coil 742 is energized, as previously described. Second housing portions 734A and 734B (collectively referred to as second housing portions 734) are coupled to first housing portion 730 via flexible housing portions 732. As with the embodiment of FIG. 5, by varying the adjusted electrical signal, a rapid movement towards and away from the recipient (as indicated by direction arrow 738) is generated, thereby providing controlled mechanical forces in the direction of the recipient.

In embodiments of the present invention, flexible housing portions 732 may be made of a variety of materials and mechanisms, now known or later developed, as will be obvious to persons having skill in the art. For example, compressible materials such as foam or silicone may be used to construct flexible housing portions 732. Furthermore, the compressible materials may be shaped, for example like an accordion, to further facilitate compression and decompression of flexible housing portions 732 in response to magnet 740 and vibration output element 744 being attracted to one another when coil 742 energizes magnet 740. In certain embodiments of the present invention, flexible housing portions 732 couples first housing portion 730 and second housing portions 734 so as to provide a sealed environment for the components housed therein.

Figure 8A:
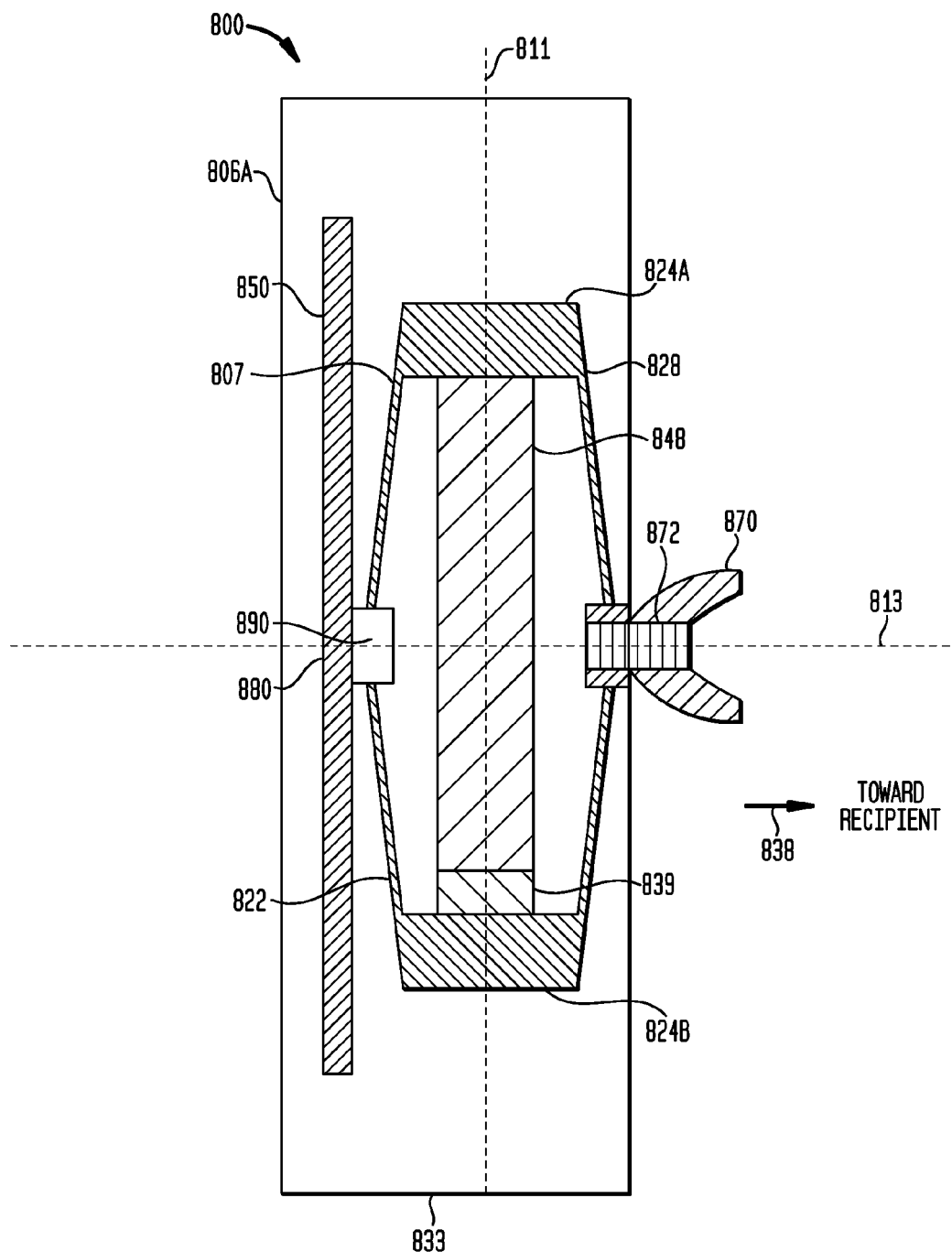
FIG. 8A is a cross-sectional view of components of a bone conduction device in accordance with embodiments of the present invention.
Figure 8B:
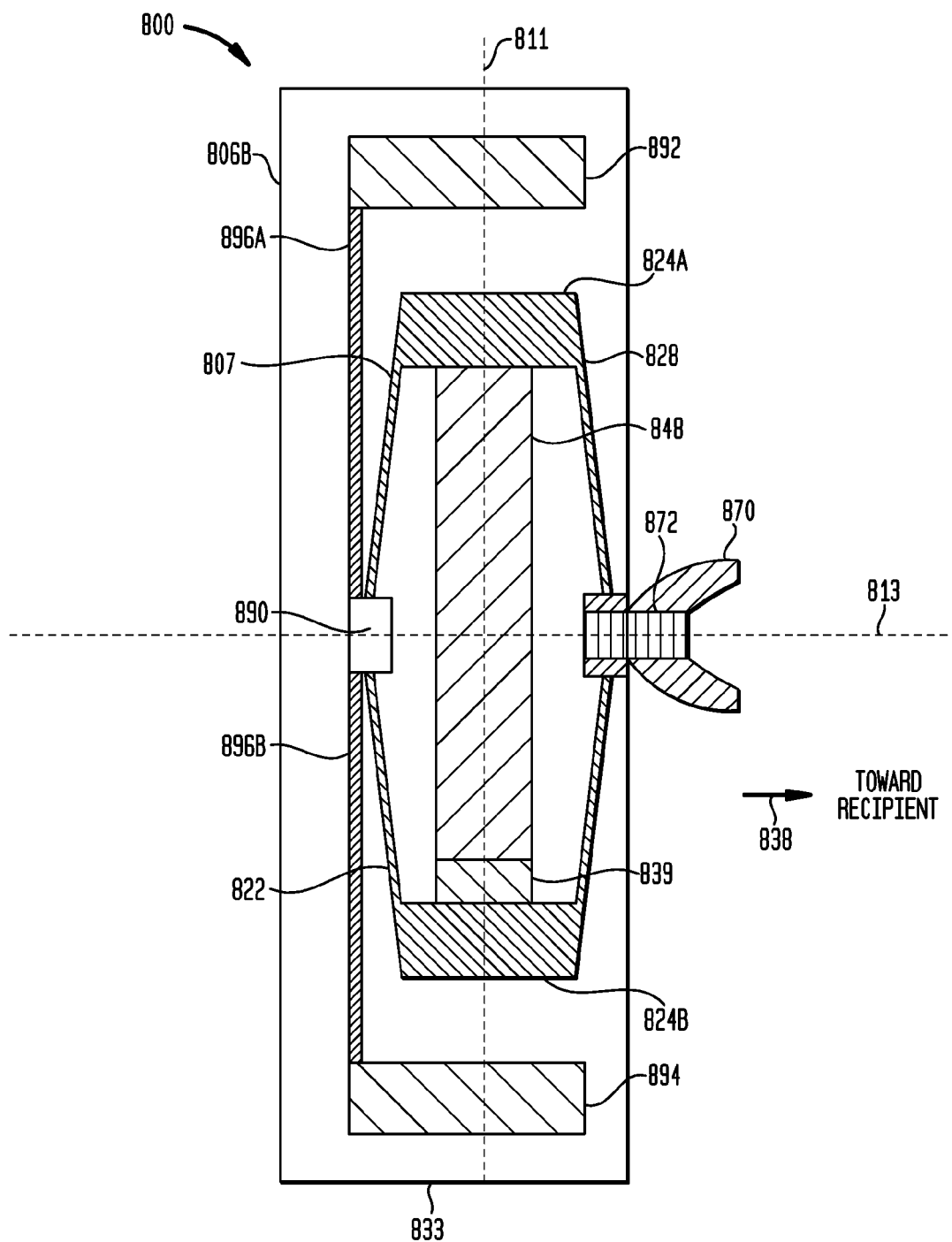
FIG. 8B is a cross-sectional view of components of a bone conduction device in accordance with embodiments of the present invention.

FIGS. 8A and 8B are cross-sectional view of components of bone conduction transducer modules 806A, 806B (collectively referred to as transducer modules 806) respectively in accordance with embodiments of the present invention. In the illustrated embodiments, transducer modules 806 each comprise a piezoelectric transducer 807 configured to convert an electrical signal representative of a sound signal received by the bone conduction device into a mechanical force. Delivery of the mechanical force to the skull causes mechanical vibration and/or movement of the recipient's skull such that the recipient perceives a hearing sensation of the received sound signal.

In the embodiments of FIGS. 8A and 8B, piezoelectric transducer 807 comprises a piezoelectric element 848 and a mechanical amplifier 828 which converts a deformation of the piezoelectric element into a mechanical deflection of one or portions of the mechanical amplifier. In the illustrative embodiments, piezoelectric element 848 comprises a plurality of layers of stacked piezoelectric material, referred to herein as a piezoelectric stack 848. Piezoelectric transducer 807 may further comprise pre-load component 839.

Mechanical amplifier 828 comprises two endplates 824A and 824B, each coupled to a separate end of piezoelectric stack 848. Mechanical amplifier 828 further comprises opposing hinge arms 822, extending between endplates 824A and 824B. Hinge arms 822 are positioned on opposing sides of piezoelectric stack 848. Each opposing hinge arm 822 and piezoelectric stack 848 define a frusto-conical shape there between. Furthermore, in the embodiment of the present invention illustrated in FIG. 8B, piezoelectric transducer 807 further comprises extension arms 896A and 896B which extend from piezoelectric stack 848 by a distance that exceeds the remainder of each of piezoelectric transducer 807 and its endplates 824A and 824B.

Following delivery of an electrical signal to piezoelectric stack 848, the stack deforms along an axis extending there through substantially parallel to extension arms 896A and 896B, illustrated as axis 811. As shown, piezoelectric stack 848 deforms by contracting along axis 811. This contraction of piezoelectric stack 848 along axis 811 causes extension arms 896A and 896B to deflect outwards from piezoelectric stack 848 along an axis substantially perpendicular to axis 811, illustrated as axis 813. As may be seen, bone conduction device 800 includes a coupling 870 connected to the device 800 via screw 872.

Deflection of extension arms 896A and 896B along axis 813 generates an output force in the direction 838 of the recipient's skull. However, in order to generate sufficient force to vibrate and/or move the recipient's skull so as to cause a hearing perception, additional mass must be coupled to amplifier 828 such that the additional mass moves when extension arms 896A and 896B deflect along axis 813. Movement of the additional mass increases the force output by transducer 807. As described below, this additional mass may take a variety of forms and may be coupled to hinge arms 822 in any number of manners.

FIG. 8A illustrates one embodiment of a bone conduction device 800 where this additional mass is provided by coupling a mass element 850 to a portion of amplifier 828. Because the force output by transducer 807 is dependent on only the mass of mass element 850, the shape, size and/or position of mass 850 is not important and generally need not take on any particular configuration. For example, as shown in FIG. 8A, mass element 850 may comprise a thin mass extending the length of amplifier 828. In other embodiments, mass element 850 may comprise a block, cylinder or any other geometric shape, optionally centered at portion 880.

As noted, the force output by transducer 807 may be altered depending on the mass of mass element 850. As such, in certain embodiments of the present invention, mass element 850 is coupled to portion 880 via a releasable coupling 890. Releasable coupling 890 is configured to permit a surgeon, clinician, recipient, etc., (collectively referred to herein as "user) to easily disconnect and/or exchange mass element 850 with a different element having a different mass, shape, etc. Releasable coupling 890 may comprise various mechanisms for coupling mass element 850 and piezoelectric transducer 807. For example, releasable coupling may comprise a magnetic coupling mechanism, a snap-lock mechanism, a compression fit-mechanism, a screw-retained structure, in addition to other mechanisms, now known or later developed, as will be apparent to a person having skill in the relevant art.

By exchanging mass element 850 in this manner, the user may customize the force output by transducer 807 for a particular recipient. For example, it may be useful to change the mass coupled to amplifier 828 depending on the skull characteristics of a recipient, or based on the hearing loss suffered by a recipient. Individuals suffering from different levels or types of hearing loss (i.e. bilateral deafness vs. single sided deafness) may require different output forces to adequately compensate for their hearing loss. As such, attachment of mass element 850 to releasable coupling 890 has the benefit that a transducer module and/or a bone conduction device may comprise all generic components and the device may be customized for a specific patient by selecting a specific shaped and/r sized mass element which is best suited for the recipient's characteristics and hearing loss.

Embodiments of the present invention further include a procedure in which a bone conduction device having transducer module 806A therein may be fitted to a recipient. During such a procedure, a surgeon may select a specific shaped and/or sized mass element which is best suited for the recipient. In such exemplary procedure, a surgeon attaches a mass element to amplifier 828 and the hearing response of the recipient is measured at plurality of frequencies and signal presentation levels by, for example, subjective user feedback, or objective measurements such as neural response telemetry measurements. A surgeon may further test a variety of mass elements in the above manner until a mass element resulting in the desired output force is found. It should be appreciated that various other fitting methods are within the scope of the present invention.

As noted above, in order to generate sufficient force to vibrate and/or move the recipient's skull so as to cause a hearing perception, additional mass must be coupled to amplifier 828 such that the additional mass moves when extension arms 896A and 896B deflect along axis 813. Movement of the additional mass increases the force output by transducer 807. FIG. 8B illustrates one embodiment of the present invention where this additional mass is provided by coupling one or more functional components to a portion of the bone conduction device 800. The functional components may be coupled to a portion of the bone conduction device 800 in any of a number of manners.

For example, in certain embodiment, as shown in FIG. 8B, one or more extension arms 896A and 896B may extend from releasable coupling 890. At the extremities of extension arms 896A and 896B, functional components 892, 894 may be suspended such that movement of extension arms 896A and 896B also cause movement of the functional components. The additional mass added by the functional components allow transducer 807 to generate sufficient output force to represent a received sound. Functional components may comprise, for example, one or more batteries, a portion of housing 833, signal processing electronics, etc.

Similar to the embodiments described above with reference to FIG. 8A, extension arms may be coupled to a portion of the bone conduction device 800 via a releasable coupling, shown as coupling 890. Releasable coupling 890 is configured to permit a surgeon, clinician, recipient, etc., (collectively referred to herein as "user) to easily disconnect and/or exchange extension arms 896A and 896B and or functional components 892, 894 with different arms and/or components having different masses, shapes, etc.

By exchanging extensions arms 896A and 896B and/or components in this manner, the user may customize the force output by transducer 807 for a particular recipient. For example, it may be useful to change the type or size of functional components 892, 894 coupled to amplifier 828 depending on the skull characteristics of a recipient, or based on the hearing loss suffered by a recipient. Individuals suffering from different levels or types of hearing loss (i.e., bilateral deafness vs. single sided deafness) may require different output forces to adequately compensate for their hearing loss. As such, attachment of different components via extension arms 896A and 896B and releasable coupling 890 has the benefit that a transducer module and/or a bone conduction device may comprise all generic components and the device may be customized for a specific patient by selecting a specific shape, size, and/or type of the functional components.

In other embodiments, one or more functional components may be releasably coupled to a portion of the bone conduction device 800 in the manners described above with reference to FIGS. 6 and 7. For example, functional component 892 and/or 894 may comprise a power module (not shown) or another functional component of transducer 806. Furthermore, functional components 892 and 894 need not comprise components having identical mass. Still further, one or more masses, which have no function other than acting as a mass, may be coupled to transducer 807 by coupling the one or more masses to releasable coupling 890 or to extension arms 896A and 896B. For example, one or more masses may be added to a particular extension arm 896A and 896B in order to counterbalance extension arms 896A and 896B where the opposite end has a functional component attached thereto. While embodiments of the present invention illustrated in FIGS. 8A and 8B have been described having piezoelectric transducers 807, it is to be understood that other embodiments of the present invention may comprise other types of transducers which generate mechanical forces.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A bone conduction device, comprising:
   a sound input element configured to receive an acoustic sound signal;
   an electronics module configured to generate an electrical signal representing said acoustic sound signal;
   a transducer configured to generate motion of a mass component based on said electrical signal so as to generate one or more mechanical forces resulting in one or more of motion and vibration of a recipient's skull thereby causing sound perception; and
   a coupler configured to releasable couple said mass component to said transducer,
   wherein one or more of the size and shape of said mass component is selectable at least partially based on a desired mechanical force to be generated by said transducer.

2. The device of claim 1, wherein said coupler comprises a snap-lock mechanism.

3. The device of claim 1, wherein said coupler is configured to screw-retain said mass component to said transducer.

4. The device of claim 1, wherein said mass component is configured to be substantially flat.

5. The device of claim 1, wherein said mass component is configured to be plate-like.

6. A bone conduction device, comprising:
   a sound input element configured to receive an acoustic sound signal;
   an electronics module configured to generate an electrical signal representing said acoustic sound signal; and
   a transducer configured to generate motion of a mass component based on said electrical signal so as to generate one or more mechanical forces resulting in one or more of motion and vibration of a recipient's skull thereby causing sound perception,
   wherein one or more of the size and shape of said mass component is selectable at least partially based on a desired mechanical force to be generated by said transducer, and
   wherein said one or more of the size and shape of said mass component is selectable based on recipient characteristics.

7. The device of claim 6, further comprising a coupler configured to releasably couple said mass component to said transducer.

8. The device of claim 7, wherein said releasable coupler comprises a snap-lock mechanism.

9. The device of claim 7, wherein said coupler is configured to screw-retain said mass component to said transducer.

10. A bone conduction kit, comprising:
    first and second mass components; and
    a bone conduction device, comprising:
      a sound input element configured to receive an acoustic sound signal;
      an electronics module configured to generate an electrical signal representing said acoustic sound signal;
      a transducer configured to have at least one of said first and second mass components positioned therein, configured to generate motion of said at least one mass component therein based on said electrical signal so as to generate one or more mechanical forces resulting in one or more of motion and vibration of a recipient's skull thereby causing sound perception; and
      a coupler configured to releasably retain at least one of said first and second mass components within said transducer,
      wherein at least one of said first or second mass components positioned in said transducer is selected at least partially based on a desired mechanical force to be generated by said transducer.

11. The kit of claim 10, wherein said coupler comprises a snap-lock mechanism.

12. The kit of claim 10, wherein said coupler is configured to screw-retain said mass component within said transducer.

13. The kit of claim 10, wherein at least one of said first or second mass positioned in said transducer is selected at least partially based on recipient characteristics.

14. A bone conduction device, comprising:
    a sound input element configured to receive an acoustic sound signal;
    an electronics module configured to generate an electrical signal representing said acoustic sound signal; and
    a transducer configured to generate motion of a mass component based on said electrical signal so as to generate one or more mechanical forces resulting in one or more of motion and vibration of a recipient's skull thereby causing sound perception,
    wherein one or more of the size and shape of said mass component is selectable at least partially based on a desired mechanical force to be generated by said transducer, and
    wherein said mass component is configured to be substantially flat.

15. The device of claim 14, wherein said one or more of the size and shape of said mass component is selectable based on recipient characteristics.

16. A bone conduction kit, comprising:
first and second mass components; and
a bone conduction device, comprising:
- a sound input element configured to receive an acoustic sound signal;
- an electronics module configured to generate an electrical signal representing said acoustic sound signal; and
- a transducer configured to have at least one of said first and second mass components positioned therein, configured to generate motion of said at least one mass component therein based on said electrical signal so as to generate one or more mechanical forces resulting in one or more of motion and vibration of a recipient's skull thereby causing sound perception,
wherein at least one of said first or second mass components positioned in said transducer is selected at least partially based on a desired mechanical force to be generated by said transducer and recipient characteristics.

17. The kit of claim 16, further comprising a coupler configured to releasably retain at least one of said first and second mass components within said transducer.

18. The kit of claim 17, wherein said coupler comprises at least one of a snap-lock mechanism or is configured to screw-retain said mass component within said transducer.

19. A bone conduction device, comprising:
- a sound input element configured to receive an acoustic sound signal;
- an electronics module configured to generate an electrical signal representing said acoustic sound signal; and
- a transducer configured to generate motion of a mass component based on said electrical signal so as to generate one or more mechanical forces resulting in one or more of motion and vibration of a recipient's skull thereby causing sound perception,
wherein one or more of the size and shape of said mass component is selectable at least partially based on a desired mechanical force to be generated by said transducer, and
wherein said mass component is configured to be substantially plate-like.

20. The device of claim 19, wherein said one or more of the size and shape of said mass component is selectable based on recipient characteristics.

* * * * *